United States Patent
Grappiolo

(10) Patent No.: US 8,764,846 B2
(45) Date of Patent: Jul. 1, 2014

(54) HIP PROSTHESIS

(76) Inventor: Guido Grappiolo, Finale Ligure Savona (IT)

( * ) Notice: Subject to any disclaimer, the term of this patent is extended or adjusted under 35 U.S.C. 154(b) by 0 days.

(21) Appl. No.: 13/276,883

(22) Filed: Oct. 19, 2011

(65) Prior Publication Data

US 2012/0095568 A1 Apr. 19, 2012

Related U.S. Application Data

(63) Continuation of application No. PCT/IT2010/000168, filed on Apr. 19, 2010.

(30) Foreign Application Priority Data

Apr. 20, 2009 (IT) .............................. RM2009A0179

(51) Int. Cl.
| | |
|---|---|
| *A61F 2/32* | (2006.01) |
| *A61F 2/36* | (2006.01) |
| *A61F 2/46* | (2006.01) |
| *A61F 2/30* | (2006.01) |

(52) U.S. Cl.
CPC ....... *A61F 2/3662* (2013.01); *A61F 2002/3625* (2013.01); *A61F 2230/0026* (2013.01); *A61F 2002/3668* (2013.01); *A61F 2002/4629* (2013.01); *A61F 2002/4619* (2013.01); *A61F 2002/30616* (2013.01); *A61F 2002/30158* (2013.01)
USPC ...................................................... 623/23.31

(58) Field of Classification Search
USPC ................. 623/23.26, 23.31, 23.35
See application file for complete search history.

(56) References Cited

U.S. PATENT DOCUMENTS

| | | | | |
|---|---|---|---|---|
| 4,404,693 A | * | 9/1983 | Zweymuller | 623/23.29 |
| 4,430,761 A | * | 2/1984 | Niederer et al. | 623/23.44 |
| 4,704,128 A | * | 11/1987 | Frey | 623/23.31 |

(Continued)

FOREIGN PATENT DOCUMENTS

| | | |
|---|---|---|
| EP | 0141022 A1 | 5/1985 |
| EP | 0677281 A2 | 10/1995 |

(Continued)

OTHER PUBLICATIONS

International Search Report issued on Sep. 29, 2010 regarding International Application No. PCT/IT2010/000168 filed on Apr. 19, 2010, 4 pages.

(Continued)

*Primary Examiner* — Bruce E Snow
(74) *Attorney, Agent, or Firm* — Gesmer Updegrove LLP

(57) ABSTRACT

The present invention relates to a hip prosthesis (1) comprising a femoral stem (20) that can be inserted within the medullar channel of a patient femur, the medial side (21) of said femoral stem (20) having, in the proximal portion (40), the shape of an arc, said femoral stem (20) being provided with substantially longitudinal lateral reliefs (60, 61), so that said stem (20) can be fixed to the bone tissue by pressure, and a prosthetic neck (30), provided with means for coupling with a morse cone type spherical head (31), said prosthesis (1) being characterized in that the cross section of said longitudinal reliefs (60, 61) has an apex portion (60'), having the lateral walls included within a first angle (c), and a base portion having the lateral walls included within a second angle (d), which is minor or equal to said first angle (c), and in that grooves (63) are provided between said longitudinal reliefs (60, 61), that can be homogeneously filled with spongious bone tissue.

17 Claims, 2 Drawing Sheets

(56) References Cited

U.S. PATENT DOCUMENTS

| | | | |
|---|---|---|---|
| 4,778,475 A * | 10/1988 | Ranawat et al. | 623/23.35 |
| 6,168,632 B1 * | 1/2001 | Moser et al. | 623/23.31 |
| 2006/0190092 A1 | 8/2006 | Fridshtand et al. | |

FOREIGN PATENT DOCUMENTS

| | | | |
|---|---|---|---|
| EP | 0709071 | A2 | 5/1996 |
| EP | 0985385 | A1 | 3/2000 |
| FR | 2868689 | A1 | 10/2005 |
| WO | 0059410 | A2 | 10/2000 |
| WO | 2010122590 | A1 | 10/2010 |

OTHER PUBLICATIONS

International Preliminary Report on Patentability and Written Opinion issued on Oct. 25, 2011, in connection with International Patent Application Serial No. PCT/IT2010/000168.

* cited by examiner

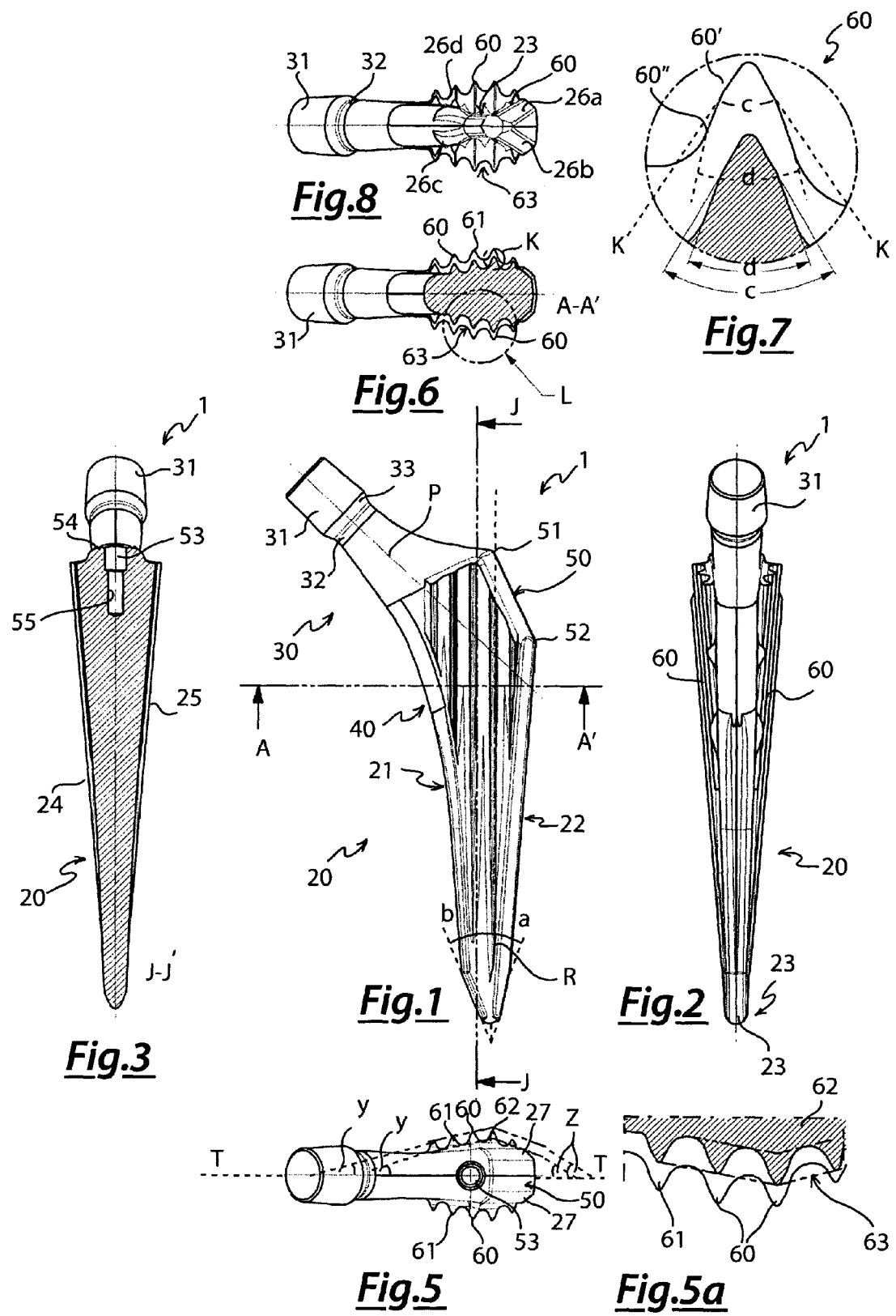

HIP PROSTHESIS

PRIORITY

This application is a continuation of International Application No. PCT/IT2010/000168 filed on Apr. 19, 2010, which claims priority to Italian patent application No. RM2009A000179 filed on Apr. 20, 2009, each of which is hereby incorporated by reference in its entirety.

BACKGROUND

The present invention relates to a hip prosthesis, More specifically, the invention concerns a prosthesis permitting avoiding rotation or sinking phenomenons, thus permitting an optimum diaphyseal blocking.

As it is well known, a hip prosthesis is typically comprised of a femur stem, to be inserted within the medullary channel of the femur on which prosthesis must be provided, comprising articulation of the interested hip, a prosthetic neck, at the end of which a head is inserted, which is part of the prosthetic device and is destined to be inserted within a cavity usually comprised of polyethylene. The head is suitable to be placed within the cotyloid cavity of the hip iliac bone, at the level of which it is usually inserted a metallic cotyle having a suitable shape.

An example of a hip prosthesis according to known technique is described in the US Patent Application no. US 2006/0190092.

A further example of known prosthesis is described in European Patent EP 0 985 385 B1, wherein the femur stem has longitudinal reliefs provided with a particular spacing in order to permit a better fixing. However, said reliefs have a cross-section not permitting an optimum osteo-integration.

One of the main problems of hip prostheses according known art is detachment of femur stem, or the removal of bone capital.

These limits make it difficult to permit possible revisions and maintenance of the same prosthesis; furthermore, standard length of femur stems complicates their use with mini-invasive techniques of treating muscle tissues, tendons and ligaments.

Moreover, standard prosthesis, if shortened, do not fully eliminate serious phenomenons of prosthesis rotation within the femur channel and stem sinking, that must be prevented following the implantation of the same prosthesis.

A further limitation of the known prosthesis is that they do not permit introduction within a medullary channel, since greater trochanter base must be removed, thus reducing preservation of bone tissue. Moreover, as it is well known, the femur is subjected to a bending moment on its proximal portion. Therefore, during the post-implantation step, in case stems are introduced with a recto or acute angle, it is necessary, for surgical reasons, to insert the femur stem after having carried out osteotomy of the femur neck and shoulder. This creates a discontinuity of the bone/prosthesis structure, since a space is created close to the contact point with the prosthesis.

It is also known that femur channel does not have a perfectly circular cross-section, but rather an oval cross-section, with a narrower or wider curvature is provided in the medial position, while larger curvature is provided in lateral position. The broken trapezoidal cross-section usually used for known femur stem, has the advantage of increasing stereo-stability, but has three main drawbacks: (i) its shape imposes four point contacts (always on the cross-section) with femur cortical bone; (ii) stem volume is often under-dimensioned with respect to femur channel; (iii) length of this kind of stem is usually too long, in order to increase its stability.

The circular section stems too are not anatomically suitable to the femur channel shape.

SUMMARY

In view of the above, it is therefore object of the present invention that of providing a hip prosthesis that can solve the above technical drawbacks, permitting an optimum osteo-integration.

It is also object of the present invention that of suggesting a hip prosthesis permitting obtaining a solid blocking within femur since the realisation of the implantation.

Another object of the invention is that of suggesting a hip prosthesis provided with a rather short femur stem, but that can distribute mechanical tension peaks on bone tissue of femur with prosthesis ensuring initial stability notwithstanding reduction of lateral dimension, so as to preserve bone capital also at the greater trochanter level.

It is therefore a specific object of the present invention to provide a hip prosthesis comprising a femoral stem that can be inserted within the medullar channel of a patient femur, the medial side of the femoral stem having, in the proximal portion, the shape of an arc, the femoral stem being provided with substantially longitudinal lateral reliefs, so that the stem can be fixed to the bone tissue by pressure, and a prosthetic neck, provided with means for coupling with a morse cone type spherical head, the prosthesis being characterised in that the cross section of the longitudinal reliefs has an apex portion, having the lateral walls included within a first angle, and a base portion having the lateral walls included within a second angle, which is minor or equal to the first angle, and in that grooves are provided between the longitudinal reliefs, that can be homogeneously filled with spongious bone tissue.

Always according to the invention, the femoral stem has a front side and a rear side on which the reliefs are arranged.

Still according to the invention, the femoral stem has a main axis, the main axis being the rectilinear line connecting the apex of the distal end of the femoral stem and the point in which the femoral stem joins with the prosthetic neck, and in that the main relief of each front and rear side, arranged in correspondence with the main axis, has a height greater than the other adjacent longitudinal reliefs.

Furthermore according to the invention, the edges of the distal end are so shaped to obtain bevellings.

Always according to the invention, a cross section of the longitudinal reliefs has an inclination of its top with respect to the symmetry axis of the prosthesis different to the inclination with respect to the body of the femoral stem, so as to improve the penetration of the femoral stem and its eventual removability.

Still according to the invention, the grooves have a cross section having a rounded concavity, in such way that they can be homogeneously filled with spongious bone tissue.

Advantageously according to the invention, a distance between the top of the longitudinal reliefs is constant, preferably equal to 4.5 mm.

Furthermore according to the invention, the femoral stem has a shape tapered towards the distal end.

Preferably according to the invention, the stem has, on its lateral side, an upper bevelling or shoulder, which has a smooth surface, shaped in such way to preserve the greater trochanter.

Always according to the invention, the shoulder comprises lateral joint surfaces, with the front faces and the rear face, the lateral joint surfaces being preferably rounded.

Still according to the invention, the prosthesis comprises upper longitudinal lateral reliefs and lower longitudinal lateral reliefs, and relevant grooves, arranged on the lateral side, so that: the upper longitudinal lateral reliefs starting substantially from an intermediate point of the shoulder and reaching a portion of the femur neck; and the lower longitudinal lateral reliefs starting substantially from the intermediate point of the shoulder as far a portion of the femoral stem.

Furthermore according to the invention, the prosthetic neck has a longitudinal axis intersecting the main axis of the femoral stem by an angle comprised between 133° and 122°, preferably equal to 133° or 122°.

Advantageously according to the invention, an arc of the proximal end has a curvature that substantially comprises the average curvature of the femur of a human being.
Always according to the invention, the femoral stem has a polygonal cross section.
Still according to the invention, the femoral stem comprises at the above a hollow, having an insertion bevelling for inserting a tool, and an internal threaded portion for coupling the tool.

Furthermore according to the invention, the stem can have a substantially trapezoidal cross-section, preferably an isosceles trapezoidal cross-section, the minor base of which is faced toward the medial face and the longer base of which is faced toward the lateral face, angles of the trapezium being bevelled angles.

BRIEF DESCRIPTION OF THE DRAWINGS

The present invention will be now described for illustrative, but not limitative purposes, according to its preferred embodiments, with particular reference to the figures of the enclosed drawings, wherein:

FIG. 1 shows a front view of a femur stem of hip prosthesis according to the present invention;

FIG. 2 shows a medial view of the femur stem of hip prosthesis according to FIG. 1;

FIG. 3 shows a section view taken along line J-J' of the hip prosthesis according to FIG. 1;

FIG. 5 shows a plan view of the prosthesis of FIG. 1;

FIG. 5a shows a particular of FIG. 5;

FIG. 6 shows a section view taken along line A-A' the hip prosthesis according to FIG. 1;

FIG. 7 shows a particular of the hip prosthesis according to FIG. 5; and

FIG. 8 is a bottom view of the prosthesis according to FIG. 1.

DETAILED DESCRIPTION

Figure 4:
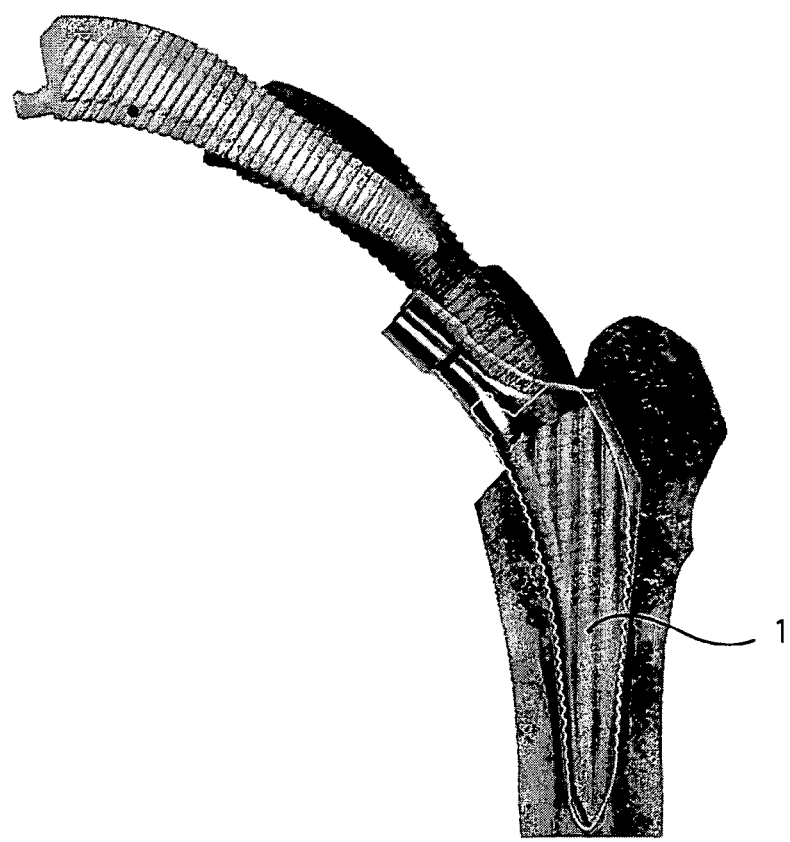
FIG. 4 shows different steps of introduction of a hip prosthesis within endo medullary channel of a femur.

In the different figures, similar parts will be described by the same references.

Making reference to FIGS. 1-3, a hip prosthesis 1 according to the invention is shown, comprising a femur stem 20, or endo medullary portion, connected with a prosthetic neck 30, or extra medullary portion.

Prosthetic neck 30 is designed to project from a prosthesized femur. Furthermore, the prosthetic neck 30 comprises at its end a morse shaped cone 31, to which a spherical head (not shown in the figures) can be coupled, usually made up of stainless steel, ceramic or cobalt-chrome alloy, suitable to cooperate with a cotyloid cavity. Prosthetic neck 30 also has a cylindrical portion 32. Morse cone 31 joins with the cylindrical portion 32 by a narrowing 33, with an inclination preferably of 45°.

Always making reference to the figures, the femur stem 20 has a medial face 21 and a lateral face 22. Further, the femur stem 20 has a diamond shaped polygonal section.

The length of femur stem 20 is such not to interfere with the femur isthmus. In fact, in case femur stem 20, due to its length, fits close to the isthmus, a stress transfer area would be provided up to that point, and thus be too distal from the area of insertion of the same stem, causing a transfer from a stem-bone interference area from proximal to distal. This adversely affects post-implantation regenerative development, with an unavoidable reduction of load on the proximal area and an overload on the distal area close to the isthmus.

The above also implies requiring that the femur stem 20 be centered both on the front plane and in the lateral stem. Femur stem 20 of prosthesis 1 does not interfere at the distal level and permits, due to the shoulder 50, the function of providing an introduction allowing a bone-prosthesis adhesion in the proximal and trochanter area and not in the distal and diaphyseal area, which will be further described in the following.

The medial face 21 of the femur stem 20 is joined with prosthetic neck 30 due to an upper or proximal portion 40 (provided on the proximal end) of the femur stem 20, with an arc having a curvature substantially including the average curvature of human femur.

Instead, lateral face 22 is shaped and has a bevelling realising a kind of shoulder 50 with a smooth surface, obtained between point 52, substantially in correspondence of the half or intermediate point (the intermediate point is defined by a normal line oriented inward of the upper or proximal portion 40 joining the point 52) of the arc obtained on the opposed portion of stem 20, i.e. medial face 21, and point 51, wherein the femur stem 20 joins with the prosthetic neck 30.

The shoulder 50 permits preserving grand trochanter after digging on the femur as carried out by a surgeon for insertion of the prosthesis 1, thus also easing insertion of femur stem 20 within the femur medullary channel.

FIG. 4 shows a mode of introduction of prosthesis 1 within an endo medullary channel of a femur thanks due to the shape of shoulder 50 and joining surfaces 27 (see FIG. 5), in combination with the curved upper or proximal portion 40. Bevelling of the lateral proximal portion of prosthesis 1 between a continuity plane between the neck and femur stem 20 permits introducing it through a neck entrance thereby permitting a rotation along neck medial cortical. Prosthesis 1 can adhere to the seat obtained by suitable tools, without creating matter spaces and discontinuities that would modify the final stress condition. The shoulder 50 further promotes a reduced, or even null, aggression of the soft parts.

Therefore, the morphology of prosthesis 1 in the lateral proximal area permits an introduction of the same by rotation with respect to neck 30, without removal of bone tissue from the trochanter. In fact, taking into consideration that the femur is subjected to a person's weight force, stressing prosthesis 1 femur head, and is subjected to a traction action of trochanter muscles (medium-gluteus) according to a direction substantially opposed to the person's weight force, it is possible to image the application of a bending moment that, in a healthy bone, is transmitted on all the femur proximal portion without discontinuities. Maintaining the basis of greater trochanter thus permits maintaining an optimum coupling of the prosthesis with bone tissue, although it is stressed by the bending moment.

Femur stem 20 is inscribed along the front plane within an imaginary triangle, the lateral side of which makes an angle a with a main axis R (that will be better described in the following) substantially placed longitudinally with respect to femur stem 20, while a medial side makes an angle b with the same main axis R. The angles a and b divide lateral face 22 and medial face 21 of said femur stem 20. Furthermore, based on the above structure, a lower or distal end 23 of femur stem 20 has an apex 23'.

The above main axis R is the line passing through the point 51 and apex 23' of distal end 23 of femur stem 20.

Femur stem 20 further has a front face 24 and a rear face 25, on which longitudinal reliefs 60 are provided, following profile of femur stem 20 and substantially extending from the proximal end to the distal end of the same femur stem 20.

Making now reference also to FIGS. 5-8, it is shown that the longitudinal reliefs 60 do not have all the same height, following a diamond shape profile on its transverse plane.

A main longitudinal relief 61, provided on each one of the front surface 24 or rear surface 25, substantially in correspondence of the main axis R of the femur stem 20, taking into consideration the reliefs 60. With respect to section line A-A', the main relief 61 is higher than the others.

The heights of other longitudinal reliefs 60 decrease both according to the lateral face 22 direction and according to the medial face 21 direction, with different slopes.

The distance between peaks of the longitudinal reliefs 60 is, in a preferred embodiment, uniform, and is equal to 4.5 mm.

Longitudinal reliefs 60 are preferably placed on a base 62, having the same profile (slope) of a peak of the longitudinal reliefs. Particularly, making reference to FIG. 5, prominence angle z and a full section angle γ are shown defining the transverse geometry of longitudinal reliefs 60.

The prominence angle z, corresponds to an intersection of a front-rear angle T plane with lines (dashed lines are shown in the figure) joining peaks of main longitudinal relief 61 with peaks of longitudinal reliefs 60 adjacent according to a lateral direction, with lines laying on or being parallel to the transverse plane A-A'.

The full section angle γ, corresponds to an intersection of the plane T with lines joining the peak of main longitudinal relief 61 with peaks of longitudinal reliefs 60, adjacent along the medial direction, with the lines laying on or being parallel to the transverse plane A-A'.

The longitudinal reliefs 60 permit, increasing torque resistance, reducing the length of femur stem 20 with respect to known prostheses, permitting a mini-invasive insertion of the same metaphyseal "press-type" kind, i.e. based on anchoring femur stem 20 with the femur bone tissue by friction.

Furthermore, the anchoring is also facilitated by the profile of hip prosthesis 1, since it permits reducing the length of the distal portion of the femur stem 20.

Grooves 63 are provided between the longitudinal reliefs 60, each one having different characteristics.

Instead, the profiles of longitudinal reliefs 60 along the transverse plane have a double slope, defined by a first and a second wall opening angle c and d, different from each other, the shaping of which is suitable to differently distribute contact forces with the bone tissue. In other words, the transverse section of each one of the longitudinal reliefs 60 or 61 has an apex portion 60' with lateral walls inscribed within the first angle c, and a base portion 60" having lateral walls inscribed within a second angle d, minor or equal to the first angle c.

The walls therefore have two different convergence angles (one angle c and the other one angle d), exerting two functions:

the peaks of the longitudinal reliefs 60 permit an optimum penetration within spongy bone tissue; and the base of each longitudinal relief 60 varies in its slope and joins at the bottom grooves 63), permitting filling spaces between the same longitudinal reliefs 60 with spongy tissue, in a homogeneous and full way. In fact, the bone tissue smoothly slides along longitudinal reliefs 60 or main longitudinal relief 61 wall, without smooth or sharp discontinuities.

In other words, the cross section of the longitudinal reliefs 60 is suitable for permitting bone tissue to homogeneously and fully (i.e. with a substantially uniform density) fill grooves 30.

The differences of the angles c and d permit increasing bone-prosthesis contact surface, as well as reducing the volume of prosthesis 1. Moreover, the contact surface increases and the transfer of load to bone tissue improves. In fact, the stress condition of bone tissue, deriving from prosthesis implantation 1 is a strongly variable conditioning outcome of articular reconstruction.

Moreover, one of variables in conditioning regeneration of bone tissue is its stress condition. All stresses (stresses and deformations) applied on the same must be within such ranges to prevent under-stresses, so that bone re-absorption would occur; or over-stresses, so that hypertrophism would occur, i.e. not controlled tissue growing, caused by the request of tissue to balance overstressing; or even reabsorption caused by an inability of supporting stress condition (biologic collapse).

Load distribution is therefore very important for success of prosthetic implant. Increase of contact surface creates a reduction of load transferred for surface unity and thus a reduction of the over-stresses risk, which is highly probable in the area of longitudinal reliefs 60.

Finally, the difference between angles c and d also permits obtaining, with the same penetration of longitudinal reliefs 60 and main longitudinal relief 61 (lug height), a reduction of prosthesis 1 volume. The above permits preserving the highest bone tissue possible.

longitudinal reliefs 60 and main longitudinal relief 61 are joined with prosthesis base 62 according to a radiused mode, thus permitting, as already stated, the homogeneous collection of bone tissue within grooves 63 or interspaces, stimulating regeneration by a uniform stressing of the same tissue. In other words, bone tissue, due to the joining of the bone tissue housing up to the base (bottom) of grooves 63 of longitudinal reliefs 60, thus avoiding discontinuities that would not permit homogeneously collecting bone tissue.

It must be taken into consideration that this joining permits having a direction of pressure exerted from prosthesis on tissue and vice versa (action and reaction principle) that varies in direction. This influences the stimulation of regeneration, since it increases the possibility that the total stress condition, generated by a stresses intensity and direction, is such to be included within a suitable range. Furthermore, it is to be taken into consideration that, with reference to the lateral plane (the one indicated in FIGS. 1-3 by section line J-J), the inclination of longitudinal reliefs 60, and main longitudinal relief 61 peak, with respect to symmetry vertical axis of said prosthesis 1 is different with respect to the one of the femur stem 20 body, in order to improve penetration of femur stem 20 and the possibly its removal.

Due to the above anchoring and structure, hip prosthesis 1 according to the invention remarkably limits sinking phenomenon and increases torque resistance of prosthesis 1, since longitudinal reliefs 60, and particularly main longitudinal relief 61, distribute along the whole prosthetic body.

Furthermore, the configuration of the longitudinal reliefs 60 as defined in the above, permits a double "press-fit" coupling, which, in the cortical-spongious and area subjected to pressure permits a better integration with bone tissue, due to the action of uniform stresses promoting long term bone remodelling. In fact, the femur stem 20 according to the present invention can be implanted without cement. In fact, its surface promotes anchoring to bone tissue due to a preferred rugosity associated with a specific treatment of titanium, material, of which the prosthesis is preferably formed.

In a preferred embodiment, the hip prosthesis 1 comprises upper lateral longitudinal reliefs and lower lateral longitudinal reliefs as discussed above, and corresponding grooves as discussed above, provided on the lateral face 22, in such a way that:
  the upper lateral longitudinal reliefs substantially start from an intermediate point of the shoulder 50 up to reaching a portion of the femur neck 30; and
  the lower lateral longitudinal reliefs substantially start from an intermediate point of the shoulder 50 up to reaching a portion of the femur stem 20.

The cross sectional shape of the femur stem 20, in a preferred embodiment, preferably is a trapezoidal shape.

Corners of the distal end are preferably shaped, so as to obtain suitable bevelled surfaces, indicated by reference numbers 26a, 26b, 26c and 26d in the bottom view of FIG. 8.

The bevelled surfaces 26a, 26b, 26c and 26d improve the congruence of the femur stem 20 with respect to the endo medullary channel (without any other sacrifice of bone tissue) and, in case it is necessary ease of removal, while saving bone tissue.

Furthermore, as may be understood, joining surfaces 27 (see FIG. 5) are provided in correspondence of the proximal part of shoulder 50, permitting a better adhesion of prosthesis 1 to cortical channel morphology.

Femur stem 20 thus has a cross section with a trapezoidal base, but corners of said trapezium (joining surfaces 27) are bevelled in their lateral part, and rounded in their medial part. These features permit to the femur stem 20 to full fill the femur channel, to have a wide resting on the lateral cortical bone and mainly on the medial cortical bone, and finally to provide rotation stability.

Stereo-stability is also increased by using different heights of longitudional reliefs 60 (with respect to the cross section) on front and rear faces.

In consideration of femur having a substantially oval cross section (wider curvature of the lateral portion), the main longitudinal relief 61 is preferably positioned in the lateral part of the faces. The main longitudinal relief 61 also offers a further resting point on the cortical bone. In this case, it is not a surface contact, but a point contact.

The longitudinal reliefs 60 and the front and rear faces of the body of the femur stem 20 are zones in contact with spongy tissue. The distribuation of contact zones between spongy tissue and the cortical bone improves the distribution of loads and at the same time stimulates spongy and cortical tissue, in order to promote osteo-integration.

Proximal portion 40 on the medial side joining prosthetic neck 30 with femur stem 20 does not have bevellings, but rather arcs (is rounded).

In order to make the use of the hip prosthesis 1 adaptable, a first embodiment of prosthetic neck 30 has axis P intersecting the main axis R of femur stem 20, with a cervical-diaphyseal angle of 133° (standard gamma), while in a second embodiment, the angle is equal to 122° (varus gamma). This permits adhering to the different human morphotypes. The angles enclose standard deviation of neck varus-valgus physiological angle, thus optimising a search of an articular rotation centre.

In other words, it is possible using two types of prosthetic necks 30, which have different measures of the cervical-diaphyseal angle, to adapt to a variety of persons.

The reconstruction of prosthesized hip anatomy is very important for success of arthroplasia of the same hip. The principle on which construction of gamma of this prosthesis 1 or implant is based on, permits covering a wide range of leg offsets and lengths.

Hip prosthesis 1 according to the present invention permits using different sizes of the femur stem 20, in order to obtain an offset and a length of a femur neck more suitable to different patient morphologies, not only choosing the head, but also choosing the size of the prosthesis 1.

Size distribution is realised in such a way that femur stem 20 remains similar from size to size, while prosthetic neck 30, i.e. the extra medullary portion, varies in terms of length and offset.

Particularly, angles a and b, which define the medial face 21 and lateral face 22, remain uniform while sizes vary. This provides that the femur stem 20 remains uniform as far as its shape and dimensions are concerned, while sizes vary. Thus, it is possible choosing the offset and length of a prosthetic neck 30, and choosing a size rather than a different device, within a limited range, one may maintain the same diaphyseal surgical preparation.

The groove 53 in the top of the prosthesis facilitates placing the femur stem 20 within a femur cavity. The groove 53 has a bevelled surface 54 adapted to ease insertion of a tool, and also has an threaded inner portion 55, in order to attach the tool for extraction of the femur stem 20 in case of revision or withdrawal.

The femur stem 20 of the prosthesis according to the present invention can be therefore easily removed without damaging bone, even when it is well Osseo-integrated, due to:
  the possibility of realising the same with a reduced length, maintaining the same mechanical fixing performances, due to the combined action of the longitudinal reliefs 60 and the main longitudinal relief 61, and of grooves 63; and
  its tapered shape due to angles the a and b, which are distally converging.

An advantage of the present invention is that said hip prosthesis can be variably used as a cephalic implant, in case of fracture of the femur neck, or it can be integrated within a prosthetic system for total arthroplasia of hip articulation. In the latter case, the stem will have to be used along with a femur head and an acetabular prosthesis.

The present invention has been described for illustrative, but not limitative purposes according to its preferred embodiment, but it is to be understood that variations and/or modifications can be introduced by those skilled in the art without departing from the relevant scope, as defined in the enclosed claims.

What is claimed is:
1. Hip prosthesis comprising
  a femoral stem that can be inserted within a medullar channel of a patient femur, said femoral stem being provided with substantially longitudinal lateral reliefs, so that said stem can be fixed to the bone tissue by pressure, and
  a prosthetic neck, provided with means for coupling with a morse cone type spherical head,
  said prosthesis being characterised in that:
  said femoral stem includes a proximal portion and a distal portion, said proximal portion including a bevelled shoulder on a lateral side and a rounded portion on a medial side, and said distal portion including a bevelled lateral tapered surface and a bevelled medial tapered surface that approach one another at a distal apex, a cross section of said longitudinal reliefs has peak portions, having the lateral walls thereof at an apex portion of the peak portions included within a first angle (c), and having lateral walls thereof included at a base portion of the peak portions included within a second angle (d), which is minor or equal to said first angle (c), and grooves are provided between said peak portions, that can be homogeneously filled with spongious bone tissue while the lug portions penetrate the spongious bone tissue, and wherein the peak portions of the longitudinal reliefs taper with respect to a longitudinally extending medial to lateral center plane (T) toward the lateral side at a first angle (z), while the peak portions of the lateral reliefs taper with respect to the longitudinally extending medial to lateral center plane (T) toward the medial side at a second angle (y) that is smaller than the angle (z), wherein said base portions of the longitudinal reliefs also taper with respect to the center plane (T) toward the lateral side at the first angle (z), while the base portions of the lateral reliefs taper with respect to the center plane (T) toward the medial side at the second angle (y).

2. Prosthesis according to claim 1, characterised in that said femoral stern further includes a front side and a rear side on which said longitudinal reliefs are arranged.

3. Prosthesis according to claim 2, characterised in that said femoral stem has a main axis (R), said main axis (R) being the rectilinear line connecting the distal apex of said femoral stem and a point in which said femoral stem joins with said prosthetic neck, and in that a peak of a longitudinal relief on the front side and a peak of a longitudinal relief on the rear side, are both arranged in correspondence with said main axis (R), and define a separation between the medial and lateral potions of the prosthesis with respect to defining the first angle (y) and the second angle (z).

4. Prosthesis according to claim 1, characterised in that said grooves have a cross section having a rounded concavity, in such way that they can be homogeneously filled with spongious bone tissue.

5. Prosthesis according to claim 1, characterised in that a distance between the peaks of said longitudinal reliefs is constant.

6. Prosthesis according to claim 1, characterised in that said bevelled shoulder has a smooth surface, shaped in such way to preserve the greater trochanter.

7. Prosthesis according to claim 6, characterised in that said bevelled shoulder is coupled to the prosthetic neck by a rounded surface.

8. Prosthesis according to claim 3, characterised in that said prosthetic neck has a longitudinal axis (P) intersecting said main axis (R) of said femoral stem by an angle of between 133° and 122°.

9. Prosthesis according to claim 1, characterised in that the rounded portion of the medial portion of the bevelled shoulder has a curvature that substantially comprises the average curvature of the femur of a human being.

10. Prosthesis according to claim 1, characterised in that said femoral stem has a polygonal cross section.

11. Prosthesis according to claim 1, characterised in that said femoral stem comprises at the proximal end, an internal threaded portion for coupling to a tool.

12. Prosthesis according to claim 1, characterised in that said stem has a substantially trapezoidal cross-section, a minor base of which is faced toward said bevelled medial tapered surface and a longer base of which is faced toward said bevelled lateral tapered surface, said medial surface is parallel to said lateral surface, wherein angles of said trapezium are bevelled angles.

13. The prosthesis according to claim 1, wherein said wherein said first angle (d) provides a rounded smooth transition to an adjacent peak to permit a homogeneous collection of bone tissue within a plurality of interspaces between the peaks, so as to stimulate regeneration by a uniform stressing of said tissue.

14. The prosthesis according to claim 1, wherein said bevelled surfaces improve congruence of said stem with respect to said medullar channel.

15. The prosthesis according to claim 1, wherein said prosthesis can be integrated within a prosthetic system for arthroplasia of hip articulation.

16. Hip prosthesis comprising a femoral stem that can be inserted within a medullar channel of a patient femur, said femoral stem being provided with substantially longitudinal lateral reliefs, so that said stem can be fixed to the bone tissue by pressure, and a prosthetic neck, provided with means for coupling with a morse cone type spherical head, said prosthesis being characterised in that:

said femoral stem includes a proximal portion and a distal portion, said proximal portion including a bevelled shoulder on a lateral side and a rounded portion on a medial side, and said distal portion including a bevelled lateral tapered surface and a bevelled medial tapered surface that approach one another at a distal apex, a cross section of said longitudinal reliefs has peak portions, having the lateral walls thereof at an apex portion of the peak portions included within a first angle (c), and having lateral walls thereof included at a base portion of the peak portions included within a second angle (d), which is minor or equal to said first angle (c), and grooves are provided between said peak portions, that can be homogeneously filled with spongious bone tissue while the lug portions penetrate the spongious bone tissue, and wherein the peak portions of the longitudinal reliefs taper with respect to a longitudinally extending medial to lateral center plane (T) toward the lateral side at a first angle (z), while the peak portions of the lateral reliefs taper with respect to the longitudinally extending medial to lateral center plane (T) toward the medial side at a second angle (y) that is smaller than the angle (z), wherein said base portions of the longitudinal reliefs also taper with respect to the center plane (T) toward the lateral side at the first angle (z), while the base portions of the lateral reliefs taper with respect to the center plane (T) toward the medial side at the second angle (y), and wherein said femoral stem has a main axis (R), said main axis (R) being the rectilinear line connecting the distal apex of said femoral stem and a point in which said femoral stem joins with said prosthetic neck, and in that a peak of a longitudinal relief on a front side and a peak of a longitudinal relief on a rear side, are both arranged in correspondence with said main axis (R), and define a separation between the medial and lateral potions of the prosthesis with respect to defining the first angle (y) and the second angle (z), and wherein said bevelled shoulder is coupled to the prosthetic neck by a rounded surface extending from the main axis (R) toward the prosthetic neck.

17. Hip prosthesis comprising
a femoral stem that can be inserted within a medullar channel of a patient femur, said femoral stem being provided with substantially longitudinal lateral reliefs, so that said stem can be fixed to the bone tissue by pressure, and
a prosthetic neck, provided with means for coupling with a morse cone type spherical head,
said prosthesis being characterised in that:
said femoral stem includes a proximal portion and a distal portion separated by a main axis (R), said proximal portion including a bevelled shoulder on a lateral side and a rounded portion on a medial side, and said distal portion including a bevelled lateral tapered surface and a bevelled medial tapered surface that approach one another at a distal apex,
a cross section of said longitudinal reliefs has peak portions, having the lateral walls thereof at an apex portion of the peak portions included within a first angle (c), and having lateral walls thereof included at a base portion of the peak portions included within a second angle (d), which is minor or equal to said first angle (c), and grooves are provided between said peak portions, that can be homogeneously filled with spongious bone tissue while the lug portions penetrate the spongious bone tissue, and
wherein the peak portions of the longitudinal reliefs taper with respect to a longitudinally extending medial to lateral center plane (T) toward the lateral side at a first angle (z), while the peak portions of the lateral reliefs taper with respect to the longitudinally extending medial to lateral center plane (T) toward the medial side at a second angle (y) that is smaller than the angle (z), wherein said base portions of the longitudinal reliefs also taper with respect to the center plane (T) toward the lateral side at the first angle (z), while the base portions of the lateral reliefs taper with respect to the center plane (T) toward the medial side at the second angle (y), and
wherein said femoral stem has a main axis (R), said main axis (R) being the rectilinear line connecting the distal apex of said femoral stem and a point in which said femoral stem joins with said prosthetic neck, and in that a peak of a longitudinal relief on a front side and a peak of a longitudinal relief on a rear side, are both arranged in correspondence with said main axis (R), and define a separation between the medial and lateral potions of the prosthesis with respect to defining the first angle (y) and the second angle (z), and
wherein said bevelled shoulder is coupled to the prosthetic neck by a rounded surface extending from the main axis (R) toward the prosthetic neck; and
wherein said prosthetic neck has a longitudinal axis (P) that intersects the main axis (R) of said femoral stem by an angle of one of 122° and 133°.

* * * * *

UNITED STATES PATENT AND TRADEMARK OFFICE
CERTIFICATE OF CORRECTION

PATENT NO. : 8,764,846 B2  Page 1 of 1
APPLICATION NO. : 13/276883
DATED : July 1, 2014
INVENTOR(S) : Grappiolo et al.

It is certified that error appears in the above-identified patent and that said Letters Patent is hereby corrected as shown below:

In the Claims

Claim 2, Column 9, line 25 delete "stern" and replace with --stem--

Signed and Sealed this
Twenty-third Day of September, 2014

Michelle K. Lee
*Deputy Director of the United States Patent and Trademark Office*